United States Patent [19]

Schoendorfer

[11] Patent Number: 5,194,145
[45] Date of Patent: Mar. 16, 1993

[54] METHOD AND APPARATUS FOR SEPARATION OF MATTER FROM SUSPENSION

[75] Inventor: Donald W. Schoendorfer, Santa Ana, Calif.

[73] Assignee: William F. McLaughlin

[21] Appl. No.: 73,378

[22] Filed: Jul. 13, 1987

Related U.S. Application Data

[63] Continuation of Ser. No. 591,925, Mar. 21, 1984, abandoned.

[51] Int. Cl.⁵ ............................................. B01D 61/22
[52] U.S. Cl. ................................. 210/90; 210/321.63; 210/321.68; 210/651
[58] Field of Search .................. 210/636, 637, 321.63, 210/321.68, 321.69, 321.87, 90, 651, 103, 650

[56] References Cited

U.S. PATENT DOCUMENTS

| | | | |
|---|---|---|---|
| 3,396,103 | 8/1968 | Huntington | 210/321.1 |
| 3,705,100 | 12/1972 | Blatt et al. | 210/23 |
| 3,795,318 | 3/1974 | Crane et al. | 210/651 |
| 3,900,290 | 8/1975 | Hornstra | 210/85 |
| 3,946,731 | 3/1976 | Lichtenstein | 210/90 X |
| 4,066,554 | 1/1978 | Guyer | 210/360.1 |
| 4,093,552 | 6/1978 | Guyer | 210/23 R |
| 4,113,614 | 9/1978 | Rollo et al. | 210/90 |
| 4,191,182 | 3/1980 | Popovich et al. | 210/651 |
| 4,294,248 | 10/1981 | de Figueiredo | 210/87 |
| 4,303,068 | 12/1981 | Zelman | 210/651 |
| 4,381,999 | 5/1983 | Boucher | 210/85 |
| 4,412,553 | 11/1983 | Kopp et al. | 210/651 |
| 4,444,596 | 4/1984 | Gortz et al. | 210/90 |
| 4,486,303 | 12/1984 | Brous | 210/85 |
| 4,490,135 | 12/1984 | Troutner | 210/87 |
| 4,493,693 | 1/1985 | Bilstad et al. | 210/90 |
| 4,535,062 | 8/1985 | Muller | 210/90 |
| 4,579,662 | 4/1986 | Jonsson | 210/636 |
| 4,790,942 | 12/1988 | Shmidt et al. | 210/321.68 X |
| 5,034,135 | 7/1991 | Fischel | 210/321.68 |

FOREIGN PATENT DOCUMENTS

0052004 5/1982 European Pat. Off.
0076665 10/1983 European Pat. Off.
3043682 1/1981 Fed. Rep. of Germany.
WO82/03568 10/1982 PCT Int'l Appl.

OTHER PUBLICATIONS

G. I. Taylor, "Stability of a Viscous Liquid Contained Between Two Rotating Cylinders," *Proc. Roy. Irish Acad.*, 1923, pp. 289-343.

A. L. Zydney and C. K. Colton, "Continuous Flow Membrane Plasmapheresis: Theoretical Models for Flux and Hemolysis Prediction," *Trans Am Soc Artif Intern Organs*, vol. XXVIII (1982), pp. 408-412.

R. J. Forstrom et al, "Formed Element Deposition Onto Filtering Walls," *Trans Am Soc Artif Intern Organs*, vol. XXI (1975), pp. 602-607.

Teddy William Wood, "Deposition of Red Blood Cells Onto Filtering Surfaces," A Thesis Submitted to the Faculty of the Graduate School of the University of Minnesota, Mar. 1974.

International Publication No. WO85/02783, Jul. 4, 1985, for "Filtration Method and Apparatus" of Josif Shmidt, PCT/US84/2094.

(List continued on next page.)

*Primary Examiner*—Frank Spear

[57] ABSTRACT

A system for filtration of matter from a liquid suspension through a membrane uses a rotor within a concentric shell rotating with a surface velocity which, together with the rotor-shell gap and suspension viscosity, establishes vigorous vortex cells about the rotor. At least one of the rotor and shell surfaces include a filter membrane. Tangential velocity components at the membrane surface constantly sweep the membrane surface to limit cell deposition tendencies while constantly replenishing the medium to be filtered. The vortex cells are established along the length of the membrane despite the constant extraction of filtrate and the resultant change in physical characteristics of the suspension.

35 Claims, 4 Drawing Sheets

OTHER PUBLICATIONS

W. Tobler, "Dynamic Filtration—The Engineering Concept of the Escher Wyss Pressure Filter", Nov./Dec. 1979, *Filtration and Separation*, pp. 630–632.

"Ultrafiltration in Rotary Annular Flow", Ph.D. Dissertation by Miguel Lopez-Leiva, Dec. 1979, Division of Food Engineering, Lund University, Sweden.

W. Tobler, "Dynamic Filtration: Principle and Application of Shear Filtration in an Annular Gap", *Filtration and Separation*, Jul./Aug. 1982, pp. 329–333.

A. K. Bhagat and C. R. Wilke, "Filtration Studies With Ultrafine Particles", Sep. 1966, University of California, Lawrence Radiation Laboratory, Berkeley, California, UCRL-16574 Preprint released for announcement in *Nuclear Science Abstracts*.

A. K. Bhagat and C. R. Wilke, "Engineering Analysis Of The Rotorfermentor", Aug. 1971, paper presented at the annual meeting of the Society for Industrial Microbiology, Aug. 29–Sep. 4, 1971, Colorado State University, Fort Collins, Colorado.

"Hydrodynamics of Annular Gap Flow Between Permeable Cylinder Walls" Escher Wyss Mitteilungen Feb. 1978–Jan. 1979, 24–30; J. Lieberherr.

Dorson, Jr. et al., Int. Appli. WO82/03567, Oct. 1982.

Lopez-Leiva, "Ultrafiltration at Low Degrees of Concentration Polarization: Technical Probabilities", 1980.

METHOD AND APPARATUS FOR SEPARATION OF MATTER FROM SUSPENSION

This is a continuation of co-pending application Ser. No. 591,925 filed on Mar. 21, 1984 now abandoned.

BACKGROUND OF THE INVENTION

This invention relates to membrane filtration of matter from liquid suspensions, and particularly to biomedical applications of such technology. It is especially relevant to, but not limited to, the separation or fractionation of the constituents of blood.

Techniques for the separation and collection of given constituents of whole blood are in wide use for many therapeutic, medical and experimental applications. Plasmapheresis (the separation of fluid plasma from the red and white cells of whole blood) forms the basis of widespread plasma storage and supply systems, and also is employed increasingly in therapeutic apheresis. Plasma is collected from individual donors by withdrawing whole blood, separating the plasma, and preferably returning high hematocrit (high cell percentage) fractions back to the donor. Plasmapheresis by centrifugal separation is widely used in laboratories but is essentially a batch process of limited convenience and commercial practicality. Continuous centrifugal separation is desired if plasma is to be collected rapidly and with minimum donor inconvenience, and in the modern state of the art this cannot be done at reasonable cost. Blood handling and collection systems must be completely sterile, which in effect requires that all elements in contact with the blood be low cost disposable components or devices. Many workers in the art have thus experimented with membrane filtration techniques, in which a membrane with suitably small pore size (e.g. 0.5 microns) is utilized to filter plasma from the blood. Because of the viscous and complex quality of whole blood, simple filtration does not suffice because deposition (clogging of pores with cellular matter) quickly decreases the efficiency of transfer through the membrane.

Recognizing these problems, a number of workers in the art have sought to utilize the shear principle so as to increase efficiency. Transport of whole blood laterally across a membrane surface which is moving relative to an opposed surface sets up shearing forces on the blood sheet, tending to keep the cellular matter in motion and to lift it away from the membrane pores, substantially reducing the deposition problem. Workers in the art have observed a generally increasing relationship between the amount of shear and the efficiency of the filtration process, with an upper limit being imposed by unwanted cell disruption or hemolysis, typically at maximum shear rates of 7,500 to 10,000/sec with prior devices.

Membrane filtration effectively appeared to have reached a practical limit with various flat membrane configurations, because of various pressure losses and flow discontinuities. In practice, a substantial membrane area has been required for such configurations, in order to enable plasma collection at a reasonable rate from an individual donor. However the membrane cost is high and the system efficiency decreases with the duration of usage. Thus the desirable objective of a low cost disposable has not been heretofore achieved with a reliably operating system.

More recently, however, a remarkable advance in blood separation technology using membrane filtration has arisen from a different structure, described in patent application Ser. No. 449,470, filed Dec. 13, 1982, by Halbert Fischel and having a common assignee. The configuration described in that patent application provides filtration rates in excess of ten times that found in prior membrane filtration devices, for a given surface area. A membrane covered spinner, having an interior collection system, is disposed within a stationary shell, and blood is fed into the space between the spinner and the shell, moving both circumferentially about the shell and along the longitudinal axis to a spaced apart exit region. A practical device, having a gap of 0.030" and a rotational velocity of approximately 3600 r.p.m., with a spinner diameter of 1" (2.54 cm) and length of 3" (7.5 cm) enables plasma to be derived at approximately 45 ml/min, and with high plasma recovery (e.g. in excess of 70%). A plasma recovery of 0.9 ml/cm$^2$/min is achieved in contrast to prior art flat plate systems providing about 0.039 ml cm$^2$/min and hollow fiber systems providing 0.–013 ml cm$^2$/min. The significant improvement in filtration efficiency thus afforded makes a low cost plasmapheresis disposable practical for the first time, and enables two to three units of blood to be transferred conveniently and quickly as high hematocrit remainder is returned to the donor.

While flow conditions existing between a rotating spinner and a concentric shell have been much studied, being termed Couette flow, the extraction of a filtrate through a membrane on the spinner represents a special case of potentially wide applicability. Generically, this configuration encompasses a number of systems in which a filter member spinning within a bath is used to prevent or limit particulates in the bath from adhering to the filter, while drawing filtrate into the interior of the spinner. Particular examples of these are shown in an article by M. Lopez-Leiva entitled "Ultrafiltration at Low Degrees of Concentration Polarization: Technical Possibilities" in *Desalination* (Netherlands) Vol. 35, pp. 125–128 (1980) dealing with the concentration of milk products, and in U.S. Pat. No. 4,184,952 (Shell Oil) dealing with the extraction of oil from basic sediment and water. However, there is nothing in these disclosures that would tend to indicate that the significant improvement achieved by Fischel in plasmapheresis would even be possible, or explain the mechanism of separation in such a system. The Fischel patent application as filed hypothesized that a "shear centrifugation" effect takes place, with centrifugal forces acting to cause migration of the cellular matter outwardly toward the stationary wall, while a plasma-rich layer resides at the surface. Limiting factors on the performance of this system were described in terms of conditions to maintain laminar flow between the spinner and the outer wall, while also exerting sufficient centrifugal force to achieve outward cell migration. Thus the application purported to distinguish from other rotating flow systems in which relative movement between two concentric cylinders causes creation of localized cellular structures, called Taylor vortices, between the walls.

Taylor vortices also have been intensively investigated in the literature and a number of devices, particularly oxygenators proposed by Brumfield, in U.S. Pat. Nos. 3,771,658, 3,771,899 and 4,212,241, have been considered that utilize such effects. Most of the investigations of Taylor vortices are concerned with theoretical aspects, and few systems, including the oxygenators, have been successfully implemented using these principles. No systems using Taylor vortices are known in which the dynamics of the fluid medium between the members are affected or altered by continuous extraction of constituents from the medium.

The situation in which a filtrate is extracted from a complex fragile living system, such as whole blood, can be seen to involve many complex factors. It is shown hereafter that the operating mode in the Fischel system does not create laminar flow under the conditions stated above, and that the withdrawal of the plasma itself generates forces substantially in excess of the centrifugal forces acting on the blood cells. While the particular plasmapheresis system of Fischel functions with the efficiency described, further improvements as to the limits and optimums of the process are made feasible by the use of configurations and operating conditions which take into account all of the dominant system requirements to establish and enhance a substantially different mode of operation.

SUMMARY OF THE INVENTION

A further improved system and method for filtering matter from a suspension are provided by establishing an operating regime, in Couette-type flow, in which the radial gap, spinner diameter, and angular velocity are selected for a given liquid suspension to establish strong but controlled Taylor vortices along the length of the spinner. The strong vortex action creates a series of adjacent annular vortex cells about the spinner and moving along the length of the spinner while alternating in direction of internal circulation. The vortex action is strong enough for the cells to substantially fill the radial gap, and matter in suspension thus is impelled in a complex path having orthogonal velocity components at both the spinner and outer wall surfaces. In accordance with the invention, matter may be filtered via a surface membrane from either the inner (spinner) surface, the outer (stationary wall) surface, or both. The velocity components at the membrane surface contribute meaningfully to the high shear rate established by relative spinner-wall motion and provide an interior sweeping motion within the radial gap that tends to clear the membrane of matter that would otherwise deposit on the membrane pores as filtrate is rapidly extracted.

Systems and methods in accordance with the invention are particularly useful in overcoming the many and difficult problems of hemapheresis systems, but are equally well suited for a wide range of other applications. The concept appears useful wherever the aggregate viscosity of the system permits establishment of strong Taylor vortices over a length of spinner despite constant filtrate extraction, and the density of solid or particulate matter within the suspension allows entrainment of the matter within the circulating vortices.

In a specific example of a filtration system and method, a vortex action is created that is well above the onset of Taylor cells but below levels at which destructive shear might occur. A membrane covered spinner having an internal filtrate collection system is separated from a concentric outer wall by a predetermined radial gap within which an augmented but substantially uniform vortex action is maintained despite filtrate extraction. Preferably the radial gap is selected to be near the upper end of the permissible range where shear and vortex forces are maximum with the other factors being adjusted accordingly. This insures that the velocity of extraction through the membrane, which tends to draw cells into the membrane, is more than counteracted by the orthogonal velocity components sweeping the membrane surface. The vortex action is not so vigorous that inward flow causes cell deposition on the membrane or outward flow causes excessive turbulence and destructive effects. The counter-rotating vortices constantly mix the matter in suspension, replenishing the supply of potential filtrate available at the membrane surface, adjacent each vortex cell. Moreover there is substantially constant advance of the cells from input to output, so that local static conditions cannot exist. Filtrate within the suspension is more mobile than the entrained cellular matter or solids and can be interchanged between vortex cells so as to tend to equalize filtrate extraction rates throughout the membrane.

Under conditions of strong but controlled vortex circulation, the tangential flow velocities can advantageously be balanced for specific purposes against radial flow velocity through the membrane. In a plasmapheresis system, for example, the transmembrane pressure and the plasma throughput ("% take") are readily determined by instrumentation devices and real time calculations. The transmembrane pressure relative to plasma throughput for a 100% efficient membrane is derived by analysis or empirical observation, to establish a reference identifying the onset of cell deposition. When the transmembrane pressure increases to or above the level at which cell deposition is imminent, separation systems in accordance with the invention reduce the filtrate throughput rate at least for a time. The consequent decrease in filtrate radial flow velocity allows the tangential flow components to free deposited cells or maintain efficiency, thus clearing the membrane and restoring system efficiency. No known filtration systems have this internal capability.

Another feature of systems in accordance with the invention is that the surface topology of the membrane is selected relative to the nature of the suspension being filtered. To enhance the vortex action and minimize occlusion of membrane by blood, for example, a smooth surfaced membrane is employed that has surface irregularities no greater than the pore size. Despite the fact that membrane surface variations may be minute in many commercial membranes, they nonetheless can hemolyze and entrap red cells while diminishing the local surface effects of vortex action. Thus superior results are achieved by employing smooth surfaced membranes under these conditions.

Other systems in accordance with the invention implant the filter membrane in the outer, stationary, wall with a number of constructional advantages and minimal reduction in operating efficiency. The stationary membrane surfaces may readily be replaced for use of the system as a separator for diagnostic applications, or for applications where the system is to be operated continuously for extended periods. In a specific example of this type of separator, the vortex flow is established by a spinner retained within a concentric split housing that can be opened to replace longitudinal filter membranes. An external magnetic drive rotates the spinner at an angular velocity that insures, relative to the gap and suspension viscosity, that strong vortices exist to provide sweeping action and freedom from clogging at the membrane. With a slightly lower extraction rate than used in an interior membrane system operating with a given spinner surface velocity, a high % take is nonetheless achieved. The velocity or gap dimension can be increased to provide a higher % take in many instances. The system has further advantages if used for diagnostic or analytical purposes because the membrane can be replaced and the unit can repeatedly be reused by rinsing the membrane between operations.

A specific example of a system for providing superior plasmapheresis operation employs maximized gap spacings for a given rotational rate, together with Taylor numbers in the range of 70 to 250 and shear rates of 7500/sec to 10000/sec maximum. Among the further aspects of the invention, pore sizes can be used that are in the range of 0.8 to 1.0 microns, these being larger and more efficient than those heretofore used. In addition, blood flow through the separation device can be against gravity if desired for specific purposes. Inasmuch as minimal membrane area is desired for low cost plasmapheresis disposals, a relatively small range of gap sizes and angular velocities is employed for achieving maximized and constant throughput rates for plasma. For example, with a 1" diameter rotor the gap dimension is held in the range between about 0.018" and 0.030" for rotor angular velocities of 3000 to 3600 r.p.m.

BRIEF DESCRIPTION OF THE DRAWINGS

A better understanding of the invention may be had by reference to the following description, taken in conjunction with the accompanying drawings, in which.

DETAILED DESCRIPTION OF THE INVENTION

Figure 1:
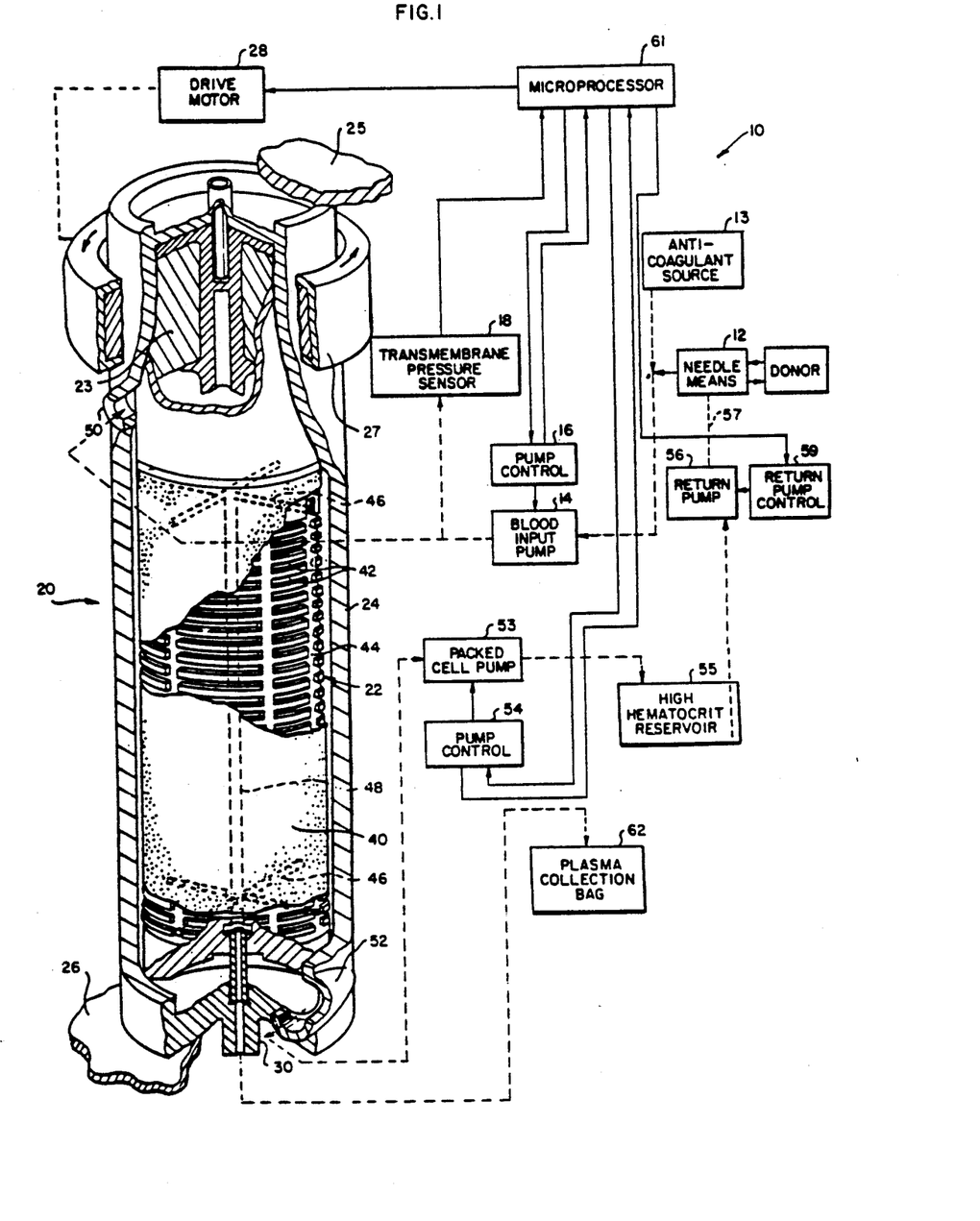
FIG. 1 is a combined perspective view, partially broken away and block diagram of a plasmapheresis system in accordance with the invention.

A plasmapheresis system 10, referring now to FIG. 1, in which the elements have been depicted only generally, provides a particularly suitable example of a blood separation system in accordance with the invention. Whole blood is taken from a donor via a needle means 12, shown as a single needle although a double needle system may alternatively be used. Disposable tubing is utilized to conduct the blood from the donor, and to combine it with a flow of anticoagulant from a source 13 (flow control for the anticoagulant being of any one of a number of known types and therefore not shown). An input blood pump 14, such as a peristaltic or pressure roller device, feeds the combined flow, when actuated by an associated blood pump control 16, to a transmembrane pressure sensor 18 and also to a disposable plasma separator device 20. The plasma separator 20 is in the form of a spinner 22 having magnetic elements 23 integral with one end and rotatable about a central longitudinal axis within a stationary housing or shear wall 24. The spinner 22 is receivable between a pair of positioning supports 25, 26 spaced apart along the central axis, and shown only generally. The upper support 25, seen only in fragmentary form, provides a positioning seat for a non-rotating upper portion of the separator device 20. At the upper end also a magnetic drive 27 (not shown in detail) encompassing and magnetically coupling to the magnetic elements 23 integral with the spinner 22, is rotated by a drive motor 28. The lower support 26 receives the lower end of the stationary housing 24 and defines an opening through which a plasma outlet 30 coaxial with the central axis may provide plasma as output.

The surface of the spinner 22 may be covered by a filter membrane 40 of a type conventionally used in blood filtration, and having surface apertures in the range of 0.1 to 1.0 microns. In the present system, however, substantial advantages are obtained by using membranes having particular physical characteristics and a pore size in the range of 0.8 to 1.0 microns, as described below. Under the membrane 40, the spinner surface is configured to define a plurality of circumferential grooves 42, interconnected by longitudinal grooves 44 which in turn communicate via radial conduits 46 with a central manifold 48. The manifold 48 is in communication, through an end seal and bearing arrangement (not shown in detail) with the plasma outlet 30.

While blood from the donor is fed into the space between the spinner 22 and inner wall of the concentric housing 24 via a tangential blood inlet 50 coupled by a flexible tubing (not shown in detail) to the blood input pump 16. A high hematocrit return flow is taken from a tangential outlet orifice 52 spaced apart from the inlet along the longitudinal axis of the separator device 20. Flexible tubing (also not shown in detail) couples the outlet 52, through a peristaltic packed cell pump 53 operated by a control 54, to a high hematocrit reservoir 55. Separator 20 operation can thereby be isolated from the donor so that alternate pump and return cycles can be used with a single needle device. Packed cells are reinfused in the donor at the needle means by a return pump 56 in a return line 57 between the needle means 12 and the reservoir 55. A return pump control 59 operates the return pump 56 at rates and times determined by the control system, which may include means (not shown) for sensing the level in the reservoir 55.

In the current state of the art, it is preferred to use a microprocessor 61 to monitor various conditions and to establish various controls, so that a number of operating modes can be established and the system can operate automatically with a minimum of operator attention. Many such features are provided in a practical example of a system in accordance with the invention, but only aspects germane to the present concept will be described, and it will be recognized that these particular features can also be provided by direct manual controls.

The principal inputs to the microprocessor 61, for purposes of the present description, are taken from the transmembrane pressure sensor coupled to the output of the blood input pump 14, and the flow rate for packed cell output established by the rate set at the packed cell pump control 54. The flow rates for the packed cell output are derived at the microprocessor 61 by counting the number of revolutions at the pump 53. Other flow rates, and the motor speed if desired, can be fed back to the microprocessor 61, but these need not be described here.

The separator device 20, the mechanical operation of which is described in greater detail in the previously mentioned Fischel application, extracts plasma from the whole blood flow, through the membrane 40. The plasma flows through the membrane 40 into the circumferential and longitudinal grooves 42, 44 on the spinner 22 surface and then into the central manifold 48 via the radial conduits 46. The collected plasma in the central manifold 48 passes through the plasma outlet 30 to a plasma collection bag 62. The typical donor supplies two to three units of plasma in thirty to forty-five minutes, this being a rate consistent with blood supply from and high hematocrit return to the donor, without discomfort or substantial danger. As noted in the Fischel application, the rate of extraction remains substantially constant. Under proper operation, the plasma is clear and golden in color, being essentially completely free of cell damage and consequent hemolysis.

Figure 2:
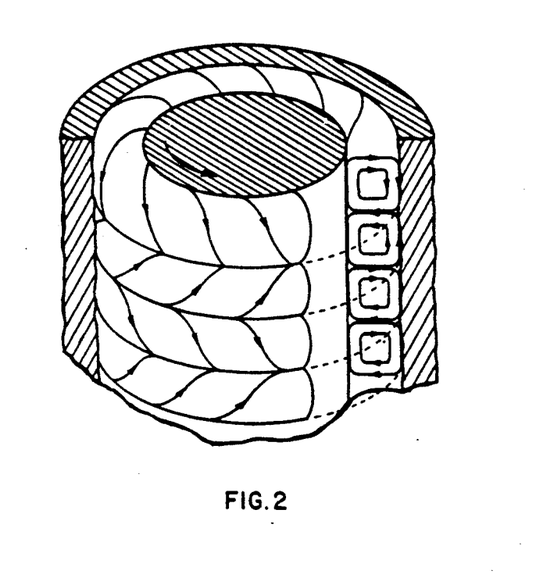
FIG. 2 is an enlarged and simplified fragmentary perspective view of a part of the plasma separation device in the arrangement of FIG. 1, showing vortex flow characteristics.
Figure 3:
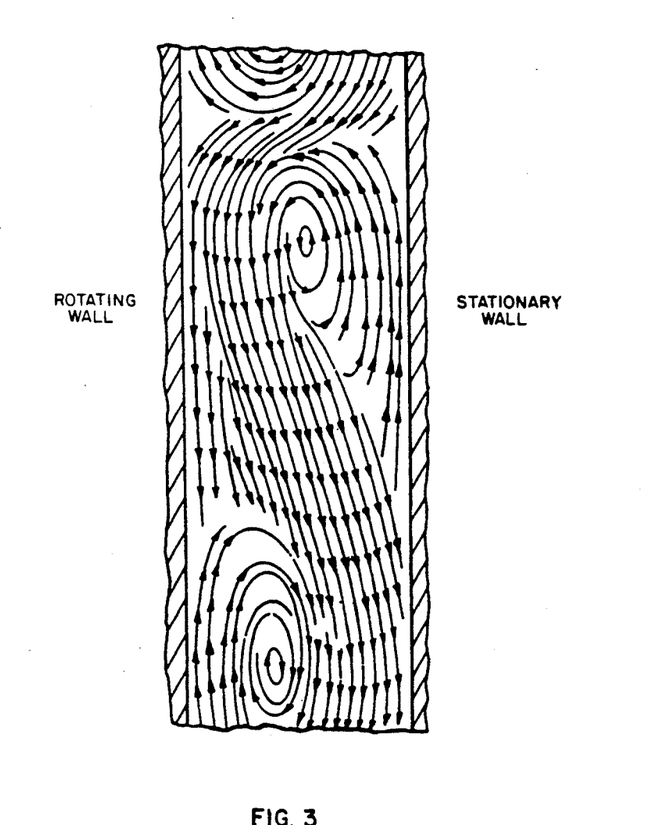
FIG. 3 is an enlarged side sectional view of the arrangement of FIG. 2, depicting vortex flow as described in the literature and as seen in operation.

It is, however, extremely important to achieve maximum reliable throughput of plasma, without trauma to the blood on the one hand or creation of a sensitive or unstable plasmapheresis procedure on the other. Further benefits can then be derived in terms of the efficiency of plasma extraction, possible reduction of the cost of the expensive filter membrane, and the amount of donor time that is required. In accordance with the present invention, applicant departs entirely from the view that a controlled laminar flow must be established, with stratification of a plasma rich layer at the membrane surface, and with outward radial migration of cellular matter in the blood. Instead, applicant induces a strong vorticity in the form of successive, alternately circulating, annuli about the spinner and occupying the gap between the spinner and the shear wall. This vortex action is of a type, referred to as Taylor vortices, first proposed by G. I. Taylor in 1923 and described by him in *Phil. Trans. Am.*, Vol. 233, pp. 289–293 in "Stability of a Viscous Liquid Contained Between Two Rotating Cylinders." Prior theoretical and computer simulation studies of the Taylor phenomenon (of which there are many) posit that the flow that is created in a Couette structure, under proper conditions, establishes a continuous sequence of annular vortex cells along the longitudinal axis of the cylinder. As seen in the fragmentary and idealized views of FIGS. 2 and 3, which are not to scale, each cell has a circulatory flow within the plane of a cross-section that is radial to the central (rotational) axis of the spinner, with the direction of circulation alternating between successive cells. The perspective view of FIG. 2 depicts the generally helical flows within an individual cell and the counter-rotation of alternate cells within the series. The sectional view of FIG. 3 represents a computer generated approximation of flows within a cross-section extending along the spinner axis and at some radius relative to the axis.

The great majority of prior studies, however, have been of stable liquid systems maintained under constant operating conditions. Proposals for practical utilization of the effect have heretofore been limited, although the theoretical investigations have been and remain extensive in character.

The Taylor number, as it is now called, was defined by G. I. Taylor as the product of the Reynolds number and the square root of the gap between the rotor and housing divided by the square root of the radius of the rotor. The vortices begin to appear, superimposed on the tangential flow induced by the relative rotation, when the Taylor number is greater than 41.3. Many of the investigations in the past have induced relative movement by spinning either the housing or the central mandrel, or both. In the examples given hereafter, only the central mandrel is spun, although the filter membrane 40 may be disposed on the spinner 22 surface or on the stationary cell. It is also feasible to utilize the vortex action and other flow conditions in a variety of other configurations and with other media, as discussed below.

Given the preferred example of the Fischel application, that of a 1" diameter spinner, 3600 r.p.m. rotation and a 0.027" gap, analysis has shown that the Fischel device actually operates in a region above the Taylor threshold. Using these operative parameters, stable and conventional laminar flow would not be established unless the gap dimension were reduced to as low as 0.010", at which value shear levels would be excessive (for the given rotational rate) and hemolysis would occur. A significant feature of applicant's invention is that vortex flow is not only permitted to occur, but is accentuated and strengthened by expansion of the vortex cell sizes to occupy substantially the entire gap region and to provide tangential movement at substantial velocity across the membrane surface.

An important consideration, in accordance with the invention, is that the entire useful surface of the membrane 40 is made to contribute to the extraction process even though the suspension changes constantly because of filtrate extraction. The vortex action is augmented to the level at which the Taylor number is in excess of 70, and preferably in excess of 100, but usually not greater than about 250, throughout the length of the filter membrane despite the substantial increase in viscosity as plasma is extracted. Because the vortex cells fill the radial gap and sweep the membrane surface in closely tangential relationship, velocity and force components of substantial magnitude adjacent the membrane 40 surface are induced that are orthogonal to the forces induced by rotation of the spinner 22. This circulating motion, coupled with convection along the spinner 22 axis, constantly seeks to remove any adherent cells from the surface of the membrane 40 and replenishes available plasma for filtration through the membrane pores. Any given point on the membrane 40 is swept in a time varying fashion by matter moving in alternately parallel and anti-parallel directions relative to the axis of rotation of the spinner. The circulatory forces that exist thus supplement the shear forces exerted on the blood by viscous drag, tangential to the spinning membrane 40 surface.

At the same time, as seen in FIG. 3, constant interchanges between adjacent cells take place, for both plasma and cellular components, although the plasma probably is transported longitudinally more readily than is the cellular matter. The interchange tends to substantially diminish any hematocrit gradient across the gap adjacent the spinner 22, although one can observe a color gradient increasing in intensity as one travels from the inlet to the outlet. Nonetheless the system achieves the desired effect of utilizing all incremental areas of the entire spinner 22 with substantially equal efficiency. Because the vortex cells are not static but are constantly moving downwardly toward the outlet 52, any given incremental area on the membrane is sequentially exposed to different vortex forces, militating against tendencies toward buildup of cell deposition. The scrolling motion of the vortex cells as the blood mass moves causes the vortex cells to be angularly disposed or slanted relative to the central axis.

The circumferential rotation within the Taylor vortex cell must not impart so high a velocity that movement inwardly toward the rotating spinner impels red cells toward the membrane with sufficient velocity to induce cell deposition on the membrane. On the opposite side, impingement of cells against the stationary outer wall cannot be so vigorous as to induce damaging turbulence. Both of these conditions can occur with strong vortex action within a range of acceptable shear, the consequences on the one hand being clogging of the pores of the membrane with a concomitant increase in transmembrane pressure and a reduction of plasma flux, and on the other the introduction of cell damage and hemolysis.

Confirmation of the existence of the vortex cells has been derived in several ways. In contradistinction to the "shear centrifugation" theory substantial plasma fluxes or throughputs have been attained utilizing a membrane disposed at the stationary shear wall as described in conjunction with FIGS. 6 and 7. It is evident that no significant plasma extraction would result if the entire mass were centrifuged forcefully enough for cells to migrate radially outwardly and to pack against the outer surface. Also, although the spinner mass appears to be uniform when viewed through a transparent shear wall by the naked eye, the use of a synchronized stroboscopic light and high speed flash photography clearly reveals the existence of the vortex cells. Under stroboscopic light, the vortices appear as in photographs depicted in the prior art, as in FIG. 7 of an article by J. E. R. Coney et al entitled "A Study Of Fully Developed, Laminar, Axial Flow And Taylor Vortex Flow By Means Of Shear Stress Measurements," in O.-Mech. Eng. Sci., Volume 21, No. 1, 1979, pp. 19-24. Further, the vortex cell formation becomes even more visible when the separator is caused to function with a mixture of minute reflection crystals in water. Experiments were also conducted in which suspended matter, in the form of hollow micro-beads, were passed through the separator mechanism in a water suspension. The system readily filtered the heavier water through the membrane, which again would not have taken place had there been a stratification of the heavier liquid outside the lighter particle matter. The theoretical existence of vortices is thus confirmed by a variety of direct evidence.

A different significant aspect of the invention relates to enhancement of the effectiveness of the vortex action and concurrent reduction of traumatic incidents arising from selective control of surface characteristics of the membrane 40. The sweeping tangential flow in a vigorous vortex as practiced herein brings fragile red cells (in a blood flow) into intimate but tangential relation to the membrane surface. Although commercially available membranes appear solid and feel smooth (at least on one side) their submicron characteristics can interact with much larger matter flowing across the surface. It is therefore preferred, in this plasmapheresis system, to employ a membrane having surface perturbations whose order of magnitude is smaller than the pore size. While a pore size of about 0.9 microns, for example, inhibits passage of red cells, a mean variation at the surface of less than that pore dimension assures a much greater freedom from capture or damage of the cells. A series of analyses using different membranes confirms that hemolysis (evidenced by increasing greater red coloration) increases in rough proportion to surface irregularities. In addition blockage by entrapment of cells appears as an increase in transmembrane pressure. While membranes can vary greatly in thickness (e.g. from 10 to 20 microns), surface protuberances and cavities should not exceed the stated relationship to pore size where blood is the medium.

Figures 7, 8:
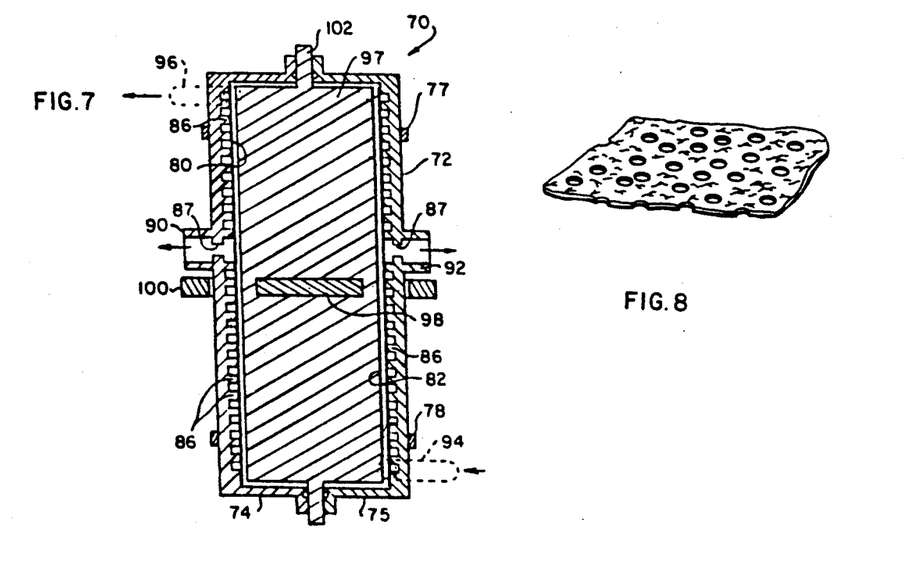
FIG. 7 is a side sectional view of the system of FIG. 6.
FIG. 8 is a perspective view, somewhat idealized and not to scale, of a fragment of a filtration membrane, showing the surface irregularities in one type of membrane.

A suitable membrane 40 is depicted in FIG. 8 as recorded on an electron micrograph. This specific membrane is a "NUCLE PORE" polycarbonate membrane; another often suitable membrane is the "Gelman Polysulfone 650 TM", but the surface characteristics of this product appear to vary, perhaps because of the use of a surface surfactant. In contrast, a nylon membrane (e.g. "Cuno 66 TM" produced by AMF) appears smooth and slippery to the touch but when examined at substantial magnification has a complex submicron surface pattern of protrusions and concavities. This type of surface is believed to generate local increases in shear stress and consequently to damage and entrap red blood cells to an extent which is evident on visual inspection. Furthermore this particular irregular surface demonstrably acts to activate platelets which cumulatively interlock and build up a barrier on the membrane, blocking the pores.

The character of the membrane surface is also important from another aspect, because if surface activation of cells commences during filtration, it continues when the rotor is stopped as during a return cycle. Consequently during the time of use of a disposable there can be a substantial loss of porous surface and marked increase in transmembrane pressure.

Another important aspect arising from the existence of the strong vortex action pertains to a technique for clearing the membrane surface of occluding cells, or maintaining efficient operation. In the system of FIG. 1, the transmembrane pressure is sensed by the pressure sensor 18 at the blood input, and a transmembrane (TMP) threshold pressure is selected based upon the sum of three pressure components, namely:

A. The centrifugal "pressure" needed to force passage of plasma from the outer edge of the spinner to the center of rotation, calculated in accordance with the following formula:

$$P_{cent} = \tfrac{1}{2} \rho \, (CPM/60 \times 2\pi)^2 (R)^2, \text{ where}$$

$\rho$ is the density of plasma.
R is the radius of the spinner
CPM is cycles or revolutions per minute B. The pressure needed to overcome pressure drop in the blood being transported through the system. This drop is not a significant factor unless the gap or tubing dimensions are reduced substantially.

C. The pressure drop introduced by the flux of plasma across the membrane. For a typical Gelman polysulfone (0.65 micron pore size) membrane, and assuming a viscosity of 1.5 times the viscosity of water, for which the pressure drop would be 0.15 mm Hg/ml/min, the resistance factor of plasma would be 0.225 mm Hg/ml/min.

The sum of the three pressure components gives a theoretical TMP which assumes that 100% of the effective membrane is functioning properly. The theoretical TMP calculation is, however, dependent on the pump rates, the hematocrit, the rpm and the diameter of the spinner as well as the flow characteristics of the membrane. However, for a 1" spinner, a gap of 0.030" and 3600 rpm, and assuming a hematocrit of 40%, and a take of 70%, a threshold of 148 mm Hg is selected as a basic reference for typical donors. This is a typical threshold level at the separator, without introducing a negative pressure force arising from gravity feed to a collection bag. In practice selection within a range of 135 to 165 mm will typically allow for operation with different donors, membranes and other variables.

If an increase of TMP above the selected threshold occurs, then the membrane may be assumed to be running at less than 100% effectiveness, so that blood cells are being deposited into the pores, or the membrane is acting to bind excessive protein, or both. Protein binding can be avoided by selection of an appropriate membrane for this specific application. However, in accordance with the invention the membrane is kept at uniform efficiency or full performance, by responsive lowering of the percentage take in one of several different modes of operation. In a steady state mode, where changes are gradual, the operative rate of the packed cell pump 53 is increased in proportion to the TMP change while holding input flow constant. The resulting amount of decrease in plasma flow is controlled so as to reduce the suction effect of the plasma flux across the membrane 40, increasing the significance of the sweeping vortex flows to maintain TMP constant. However, other modes of operation are feasible for specific TMP variations. If TMP rises quickly or a predetermined amount, then % take can be reduced substantially by an incremental amount, so that the tangential vortex cell forces act to dislodge cells or protein from occluded pores. In practice, a 6 mm Hg variation in TMP (approximately 4% increase) can be compensated for by a temporary reduction of 10% in percentage take. Only a temporary reduction in plasma flux is needed, because the cleansing effect is seen very quickly. Sufficient tangential circulation is provided by the unique combination of rotor gap radius and surface velocity to remove lodged cells and proteins in only a few seconds. In other words the cleansing action is vigorous enough to make the great majority of occlusions reversible. If the increase in TMP is too large and sudden, or if the % take reduction is too large (e.g. 70%), the system may simply be shut down and checked.

The function of shear in separation of blood components has been widely studied in the literature, and is regarded as essentially generating a lift force on cellular matter away from the membrane filter in a shear field. An article by Forstrom et al, entitled "Formed Element Deposition Onto Filtering Walls," in *Trans. Am. Soc. Art. Int. Organs*, XXI, 1975, pp. 602–607 seeks to quantify the onset of cell deposition by defining a deposition parameter in the following terms:

$$\sqrt{v}\ U_f\lambda/R2S^{3/2}$$

Where $v$ is the viscosity, $U_f$ is the filtration velocity, R is the diameter of the cell, S is the wall shear rate, and $\lambda$ is a concentrate factor dependent upon the hematocrit.

Forstrom et al state that if the value of the deposition parameter is greater than 0.343, cell deposition on the filter will occur if shear alone is the effective agent. In actuality, they found, by reviewing empirical studies, that deposition actually occurred in practical devices when the value of the deposition parameter became greater than 0.15. This was determined from published reports at the critical point where filtration velocity begins to decrease due to occlusion of pore in the filter. Systems in accordance with the invention, however, exhibit practical results that are far above the theoretical barrier proposed by Forstrom et al. A filter having 36.9 cm$^2$ of membrane provides a plasma take of 45 microliter per minute, giving a filtration velocity of 0.020 cm/sec (for 75% take of 40% hematocrit blood at 100 ml/min input). Using $\lambda=17$ with a hematocrit at 40, a value of R (the red cell diameter) of approximately 4.2 microns and a shear equal to 7500/sec, the Forstrom et al deposition parameter calculates to 0.594. Filtration without excessive cell deposition under such conditions would not, according to the Forstrom et al studies, be theoretically possible and should be even less feasible when compared to prior empirical work.

Figure 4:
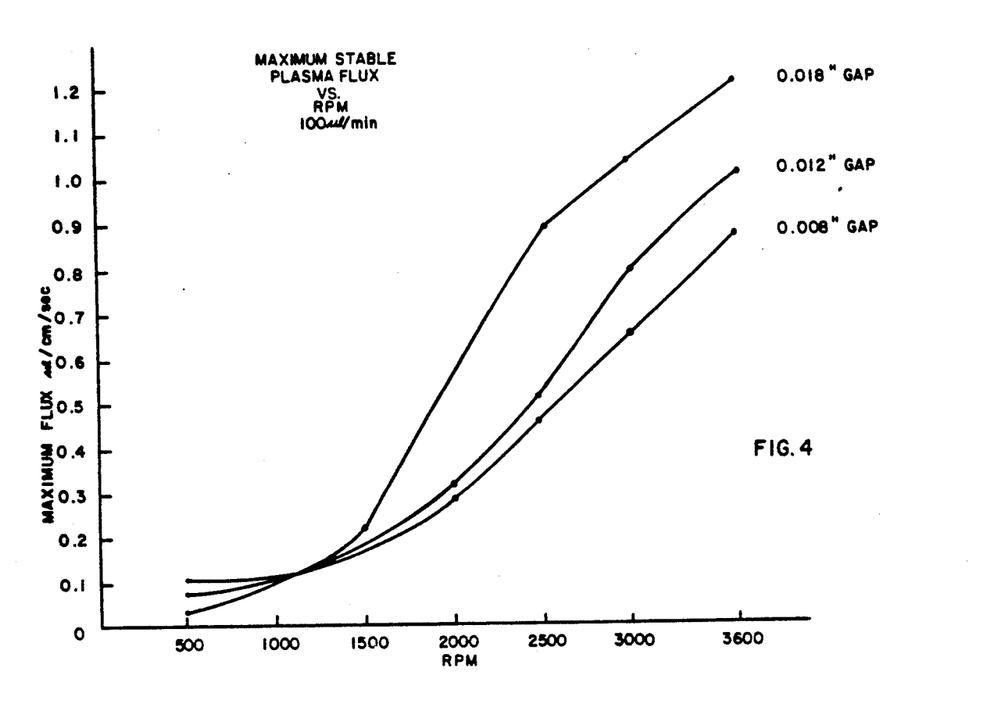
FIG. 4 is a graph showing changes in plasma delivery for given input flow, with changes in the relationship between gap and angular velocity for a given size spinner.

Consequently, systems in accordance with the invention utilize an entirely different filtration mechanism and provide previously unobtainable increases in plasma flux, with respect to increase in shear. These increases may be seen from FIG. 4, which depicts the maximum stable plasma flux in relation to angular velocity for a given blood flow (100 ml/min). The curves represent the variations encountered as angular velocity is increased for different gap sizes under the otherwise stated conditions of gap, rpm and diameter. Up to certain levels the rate of increase is substantially linear, but thereafter the rate of increase follows a steeper slope. In point of fact, the region at which the rate of increase in plasma flux rises to a higher slope can now be identified as the region of onset of the Taylor vortices. Using the previously stated Taylor equation to determine the onset of vortex cells, Taylor flow begins in the 1100–1250 r.p.m. range for the 0.018" gap, at 2600 r.p.m. for the 0.012" gap and at above 4600 r.p.m. for the 0.008" gap. Although the shear rate of the smaller gap is substantially higher, so that plasma flux should theoretically be greater if shear rate is the predominant factor, this is the case only where the rpm's are low enough to be below the Taylor instability for the gaps shown in FIG. 4. Below 1000 r.p.m., for example, the smaller gap has superior plasma flux. In contrast, the larger gap provides significantly more plasma flux, by a factor of several times, when vortex cells are properly established and have amplitudes that fill the gaps and provide vigorous cell circulation. In preferred examples, present systems operate at a Taylor number in the range of 180–200.

Donnelly et al in "Experiments On The Stabiity Of Viscous Flow Between Rotating Cylinders, VI, Finite-Amplitude," *Proc. Ray Soc.*, London, Volume 283, 1965, pp. 531–546 established that the amplitude of the Taylor vortex varies as the square root of the difference between the Taylor number at the operating rpm and the critical Taylor number. Donnelly et al, however, used a slightly different formulation for the Taylor number where the Taylor number is proportional to the square of the rpm, so that a direct comparison to values derived from the previously stated equation are not feasible. Nevertheless, the amplitude of the vortex cells increases with the Taylor number, the cells forming first at the rotating wall and expanding outwardly to fill the radial gap. When the vortex cell substantially fills the gap the action of viscous drag at the spinner surface provides local circumferential forces that are much greater than comparable forces at the stationary outer wall. The vortex cell circulation provides sweeping movement in the orthogonal direction at both walls, and it appears that this also is greater at the moving wall than the stationary wall. Vortex cell circulation at the outer wall can be increased to the level originally existing at the inner wall by increasing the rotor rpm. Either or both of the walls can include a filter membrane to achieve greater filtration efficiency than flat plate and other prior systems.

Figure 5:
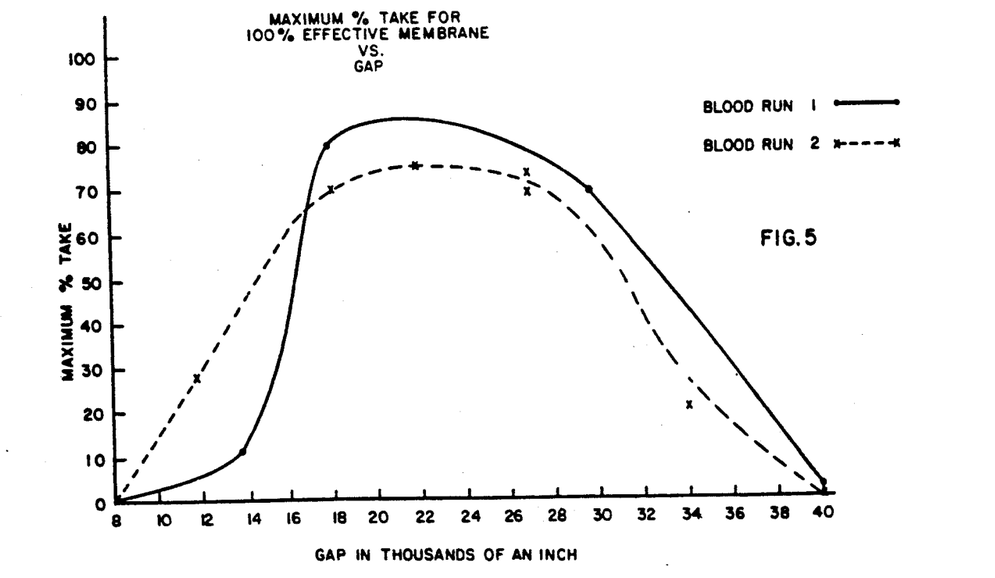
FIG. 5 is a graph showing plasma flux changes for different gap sizes, other factors remaining constant.

Because the amplitude of the Taylor vorticity increases more quickly than the shear rate as the rpm increases, the beneficial effects of Taylor vorticity provide significant contribution to the high increase in plasma flux. Relatively larger size gaps provide an increase in Taylor vortex amplitude from a lower rpm threshold region and consequently a stronger vortex action at an acceptable shear rate. There is, however, a limit at which vorticity overpowers shear, with detrimental effects. This is primarily due to the radial inward tangential forces exerted during strong vortex action, which tend to cause cell deposition on the moving membrane. When this occurs, there is a decrease in the plasma flux, and an increase in the transmembrane pressure. As illustrated in FIG. 5, the use of a large gap size, 0.040″, results in just such a diminution of performance. FIG. 5 shows variations in percentage take relative to gap size, given a rotational rate of 3600 r.p.m. It can be seen, from this Figure, that characteristics drop off substantially at gap sizes in excess of 0.030″. Clogging of the membrane requires the system to attempt to force filtration and substantially increases problems with cell damage.

A different limiting aspect is the cell disruption which can occur if vortex action is too strong, by virtue of radially outward movement of cells with such velocity that they impinge on the stationary wall, to cause hemolysis. This apparently, however, will occur subsequent to the cell deposition problem in most instances.

Hemolysis is to be avoided or kept to a minimum in plasmapheresis systems in accordance with the invention, but it must be recognized that there is no strictly defined value or limit as to the amount of permissible cell damage. Objective operative criteria, such as the shear level, are not precise determinants of whether an unacceptable level of hemolysis will be introduced in these dynamic systems. Shear limits for flat plate devices were previously considered to be in the range of 7500 sec, but present systems using vortex cell action have operated without significant hemolysis at in excess of 12,000/sec.

Figure 6:
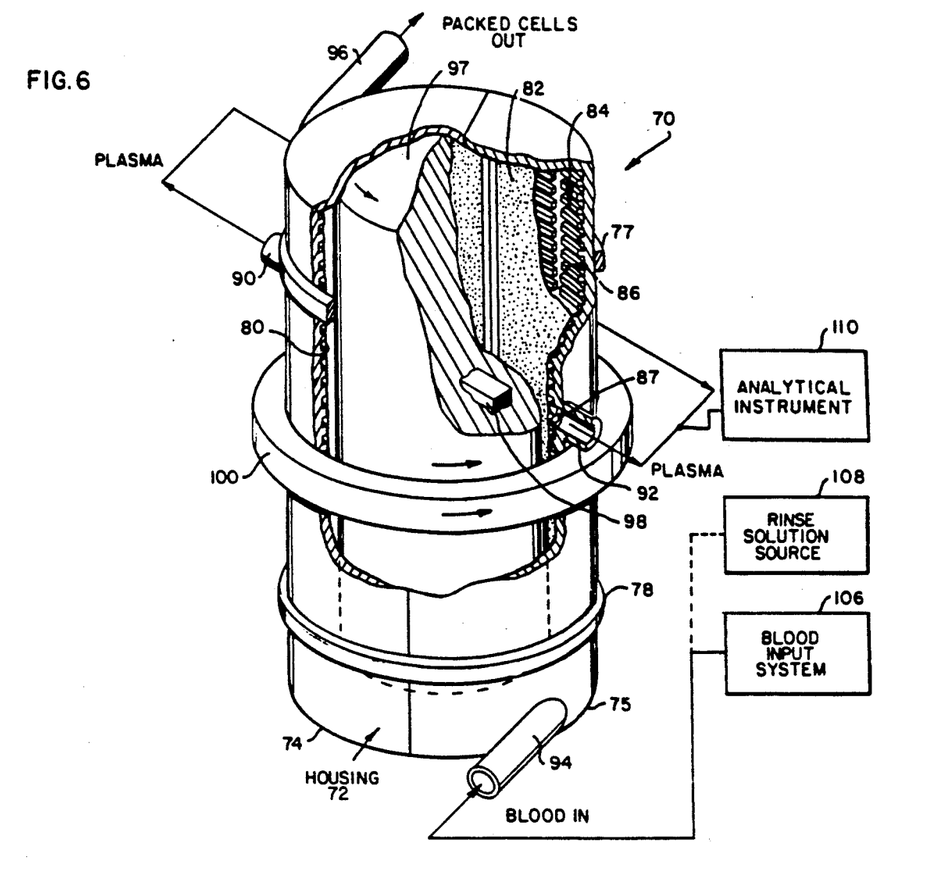
FIG. 6 is a perspective view, partially broken away, of a different example of a system in accordance with the invention utilizing a stationary membrane.

The same principles of vortex action may be utilized in conjunction with a substantially different configuration and application, as depicted in FIGS. 6 and 7, to which reference is now made. This comprises a separator device 70 for diagnostic and other analytical applications, wherein small samples may be taken and separated into constituents for individual analysis. The device of FIGS. 6 and 7 also pertains to blood separation, and the usage of separated plasma or serum, although in a diagnostic procedure. However, the principles of construction and operation will be recognized by those skilled in the art as being applicable to other separated constituents and to entirely different liquid suspensions as well.

In the separator device 70 of FIGS. 6 and 7, the cylindrical housing 72 is constructed as a separable member so that access can be had to the interior. In this example the housing 72 is formed as a pair of split halves 74, 75 having integral top and bottom end portions providing a substantially enclosed cell when joined together. The split halves 74, 75 are held together by retainers, such as clamping rings 77, 78. Seals (not shown) may be disposed between the abutting surfaces of the split halves 74, 75 as long as the concentricity of the interior surface is maintained. The inner wall of each split half 74, 75 is defined by one or more removable filter membranes 80, 82 attached as by a strippable adhesive to the adjacent lands 86 on a network 84 of grooves in the inner surfaces of the housing, these groove networks 84 in each half 74, 75 providing communicating paths through radial orifices 87 for plasma or serum flow between the inner surface of the membrane 80 or 82 and an outlet port 90 or 92, respectively. The outlet ports 90, 92 for filtrate are connected together to provide effluent for fractionation or for analysis by associated instruments. As with the system of FIG. 1, the conduit system under each membrane 80 or 82 provides adequate interconnected flow area to avoid the introduction of substantial impedance to flow of filtrate to the appropriate outlet port 90, 92. The membranes 80, 82 may be removed and replaced by detaching them from the adhesive backing, which need not be strong in view of the fact that the housing 72 and membranes 80, 82 are stationary. However, the adhesive may also be dissolved by chemical means and a new adhesive applied, or a mechanical attachment structure may alternatively be utilized as long as the concentricity of the inner housing face is maintained. It will be appreciated that other types of internally accessible housing structures, including a chemical arrangement, removable end covers and the like, may be employed for different applications.

The whole blood inlet 94 for this structure is coupled tangentially to the housing inner wall at a lower region of the housing, while the outlet 96 is positioned tangentially to the inner wall adjacent an upper end of the housing 72. Within the housing 72 is mounted a cylindrical spinner 97, having an internal magnetic member 98 mounted intermediate its ends. The spinner may be a smooth, plated surface member having an outer diameter providing the chosen gap dimension relative to the inner wall of the housing 72 defined by the membranes 80, 82 and interconnecting housing wall segments. The end surfaces of the spinner 97 are also spaced apart from the end surfaces of the housing 72 by a predetermined amount. The entire housing, in its mid region, is encompassed by a rotatable magnetic drive 100 arranged in operative relation to the magnet 98 within the spinner 97. The drive is positioned with a slight vertical displacement from the magnetic element 98, so as to tend to bias the spinner 97 upwardly and reduce the force of gravity acting against the bottom end wall of the housing. End bearings 102, 103 support the spinner 97 for rotation about the central axis.

A blood input system 106, which may comprise not only a source of whole blood but also a source of anticoagulant and saline solution if desired is coupled to the blood input to the system. A source of a rinsing solution 108 is alternatively coupled to the same input 94, the rinsing solution being substituted manually or automatically for the blood input. Plasma or serum filtered through the system is passed from the outlet 96 to an analytical instrument 110. Typically, the whole blood sample need only be sufficient in size to enable a period of stable extraction of filtrate for a long enough time to obtain an adequate plasma or serum sample (typically in the range of 5 to 30 milliliters).

The operation of the system with whole blood input is again based upon establishment of enhanced vortex flow throughout the entire length of the filter membranes 80, 82. To this end, the magnetic drive 100 synchronously rotates the inner spinner 96 through its magnetic coupling with the magnetic element 98 at a rotational velocity in the range of 3600 r.p.m., it being assumed that the spinner again is approximately 1" in diameter. Using a gap of 0.018 to 0.030", suitably adjusted for blood viscosity and other conditions, vortices are created that fill the radial gap between spinner 97 and housing 72. The existence of vigorous vortices that entirely fill the gap is more critical when the membrane surface is static than in the example of FIG. 1. Because the vortices start near the spinner surface and grow outwardly until they sweep the outer wall it is desirable to insure that viscous damping losses at the stationary wall do not prevent suitably vigorous vortex action at the outer surface. Thus the Taylor number is increased 5-10% over the values previously given for the FIG. 1 system, as by increasing the rotational speed. No hemolysis is observed when this change is made. The centrifugal displacement effects imparted by the rotation of the inner spinner 97 that tend to deposit cellular matter and other heavier matter on the surface of the membranes 80, 82 are overcome by the sweeping vortex motion at the membrane surface.

Practical systems in accordance with this example have achieved plasma filtration rates with average hematocrit (38-44% blood) far in excess of rates achieved by the best parallel plate technology previously known. The plasma flux for stable output without evidence of pore clogging was some 5-10% less than the 70% take and 39-43 ml/min rate achieved by the system of FIG. 1 for a 1" spinner. Plasma throughput was maintained without substantial diminution in properties during the extraction of 2-3 units (500-750 ml) of plasma. The plasma take is stable and amenable to achieving higher throughput by use of higher spin rates or other variables. The effective membrane area can be relatively increased because the membrane being stationary needs only enough supporting surface to be held concentric. Consequently, this system demonstrates further that the vigor of the augmented vortex condition and the sweeping action imparted by the orthogonal flow components at the membrane surface, have not only established a new filtration approach using high shear but that it also incorporates a significantly effective cleaning action.

With stationary membranes 80, 82 about the spinner 97, the system of FIG. 1 can provide successive samples of relatively small amounts of filtrate from inputs provided via the whole blood system 106 from many different sources. In a diagnostic system, where the characteristics of the plasma or serum alone are of concern, contamination is not a problem and the surface cleaning effected by the vortex action can maintain high filtration efficiency for a substantial period of time. Alternatively, saline solution from the input system 106 can be provided between whole blood samples to effect some clearing of the system, or as a further alternative the membranes 80, 82 may be cleaned by use of rinse solution from the source 108. When filtration efficiency drops in unrecoverable fashion below a selected level, the system need only be stopped, the housing 72 emptied, and the housing 72 then opened and new filter membranes 80, 82 used to replace the previously used elements.

In the example of FIGS. 6 and 7, passage of whole blood is from a lower input to a higher output, but the essential vortex action and scrolling advance of the vortex cells are unimpeded even though the net flow proceeds upwardly against gravity. As in the prior example the vortices do not remain fixed but translate upwardly in continuous fashion, thus constantly sweeping incremental areas of the surface of the filter membranes.

A number of other variations of this system, including its use for the concentration of red blood cells or platelets, will present themselves to those skilled in the art. The separator device may be fabricated as a low cost disposable, for diagnostic or conventional plasmapheresis applications. The housing structure for a disposable unit dealing with small blood samples may be configured so as to provide a retainer chamber for the packed cell output, enabling the unit, including the waste blood, simply to be disposed of following collection of the needed amount of filtrate.

While a number of forms and variations in accordance with the invention have been described it will be appreciated that the invention is not limited thereto but encompasses all modifications and expedients within the scope of the appended claims.

What is claimed is:

1. A system for filtering a cellular suspension, comprising:
    a stationary housing body having a hollow interior and an inner surface;
    rotor means rotatable within the housing body, the rotor means having an outer surface spaced from the inner surface of the housing body;
    means for feeding the fluid suspension into the space between the rotor means and the inner surface of the housing body;
    microporous filter membrane means disposed on the inner surface of the housing body for passing the filtrate to the inner surface of the housing body;
    conduit means in the housing body in communication with the inner surface of the housing body for collecting filtrate passing through the filter membrane means; and
    means coupled to the rotor means for driving the rotor means at a rate selected to establish annular vortices about the rotor means substantially filling the space between the rotor means and the housing body.

2. A system for filtering a cellular suspension, comprising:
    a housing body having a hollow interior and an inner surface;
    rotor means rotatable within the housing body, the rotor means having an outer surface space from the inner surface of the housing body;
    means for feeding the cellular suspension into the space between the rotor means and the inner surface of the housing body;
    filter membrane means on at least one of the inner surface of the housing body and the outer surface of the rotor means;
    conduit means in communication with the filter membrane means for collecting filtrate passing therethrough;
    means for driving the rotor means at a rate selected to establish annular vortices within the space between the rotor means and the housing body substantially filling the space between the rotor means and the housing body;

means for sensing the transmembrane pressure;

controllable means for maintaining a desired filtrate extraction rate through the membrane means; and means responsive to the sensed transmembrane pressure for reducing the extraction rate of filtrate while maintaining the vortex action when the transmembrane pressure rises above a calculated value to clean the filter membrane means by action of the annular vortices.

3. The invention as set forth in claim 2 above, wherein the membrane has a porosity in the range of 0.1 to 1.0 microns.

4. The invention as set forth in claim 2 wherein the cellular suspension is whole blood and the filtrate is plasma, and wherein the calculated transmembrane pressure value is no greater than about 165 mm Hg.

5. The invention as set forth in claim 2 wherein said means for reducing the filtrate extraction rate includes means for increasing fluid flow through the space between said rotor means and the inner surface of the housing body when the transmembrane pressure exceeds the calculated value, thereby causing the desired reduction in filtrate flow rate.

6. The invention set forth in claim 2 wherein the membrane comprises orifices of a predetermined nominal dimension and wherein the surface perturbations of the membrane are less in magnitude than said predetermined nominal dimension and wherein the Taylor number in the range of 180 to 220.

7. The invention set forth in claim 2 wherein the membrane is on the inner surface of the housing body.

8. The invention set forth in claim 2 wherein the membrane is on the outer surface of the rotor means.

9. The invention set forth in claim 2 and further comprising:

a source of rinsing fluid; and means communicating with the space between the rotor means and housing body and with said source of rinsing fluid for temporarily introducing said rinsing fluid into said space while simultaneously temporarily reducing the input of blood suspension into the space while maintaining the Taylor vortices in the space to assist in clearing the membrane and restoring an efficient filtering action.

10. A blood constituent filtering system of the type which, in operation, produces Taylor vortices within a gap area disposed between relatively rotating generally cylindrical surfaces, at least one of which includes a blood constituent filtering membrane to filter out a blood constituent and for passing a filtrate therethrough, said system including:

first means for detecting the onset of filter membrane pore clogging by cellular blood constituents; and second means for controlling at least one operating parameter of the filtering system to cause cleaning of the clogged pores by the sweeping action of blood constituents entrained in said Taylor vortices and passing adjacent said filtering membranes.

11. A blood constituent filtering system as in claim 10 wherein said first means comprises means for monitoring the fluid pressure at the inlet to said gap area and wherein said second means comprises means for reducing the flux of filtrate in response to monitored pressure.

12. A blood constituent filtering system as in claim 11 wherein:

said monitoring means detects the transmembrane fluid pressure across said filter membrane; and wherein said second means reduces the plasma flux passing through said filter membrane in response to transmembrane fluid pressure in excess of about 165 mm Hg.

13. A blood constituent filtering system as in claim 10 wherein said fluid membrane comprises orifices of a predetermined nominal dimension and wherein the surface perturbations of the filter membrane are less in magnitude than said predetermined nominal dimension and wherein the Taylor number is in the range of 180 to 220.

14. A blood constituent filtering system as in claim 10 wherein said filter membrane is disposed radially outwardly with respect to a rotating spinner member.

15. A blood constituent filtering system as in claim 10 further comprising:

a source of rinsing fluid; and a further fluid inlet means communicating with said gap area and with said source of rinsing fluid for temporarily introducing said rinsing fluid into said gap while simultaneously temporarily reducing the input of blood constituents maintaining said Taylor vortices in the gap area to assist in clearing the membrane and restoring an efficient filtering action.

16. A blood constituent filtering system as in claim 10 wherein the filtering membrane comprises a membrane having a surface with deviations less than a predetermined pore size, and the system includes means for sensing the transmembrane pressure, controllable means for withdrawing unfiltered blood constituents fed into the gap area and means responsive to the sensed transmembrane pressure for increasing the rate of withdrawing unfiltered blood constituents to enable internal cleaning of the filtering membrane by the vortex action.

17. A blood constituent filtering system as in claim 10 wherein said filter membrane is located on the rotating spinner.

18. A system for filtering plasma from blood with a disposable unit, comprising:

a disposable housing body including a rotor therein, at least one of the housing and rotor having a membrane filter thereon with a pore size in the range of 0.1 to 1.0 microns, and plasma conduits therein for conducting plasma to a plasma outlet, the rotor including magnetic means therein, the housing body being spaced apart from the rotor to define an annular gap and including blood inlet means leading into the annular gap, spaced apart cell concentrate outlet means communicating with the annular gap, and plasma outlet means communicating with the plasma conduits;

magnetic drive means exterior to the housing body and magnetically coupling to the magnetic means in the rotor for rotating the rotor at a rotational velocity selected, relative to the diameter of the rotor and the annular gap to establish a Taylor number of 70 to 250 throughout the annular gap with a shear rate below 12,000/sec;

means coupled to the blood inlet means for feeding blood into the annular gap at a predetermined rate;

pressure sensor means communicating with the annular gap for sensing the transmembrane pressure of the blood in the annular gap;

means responsive to the transmembrane pressure for comparing the transmembrane pressure to a threshold pressure determined primarily by the pressures required to overcome centrifugal forces, system pressure drop, and plasma flux across the membrane, and generating a responsive control signal when the transmembrane pressure exceeds the comparison; and means responsive to the control signal for varying at least one flow rate in the system apart from the predetermined inlet rate to maintain the Taylor number in the range of 70 to 250 while reducing the tendency of blood cells to clog the membrane.

19. The system as set forth in claim 18 above, wherein the system further comprises a controllable packed cell pump coupled to the cell concentrate outlet means in the housing body responsive to the control signal, and wherein the cell concentrate rate is increased in response to a transmembrane pressure in excess of the threshold, to reduce the plasma flux across the filter membrane.

20. The system as set forth in claim 19 above, wherein the conditions of blood viscosity, annular gap dimension, rotor diameter and rotational rate establish Taylor vortices in the blood in the annular gap, wherein the reduced plasma flux enhances the sweeping action of the Taylor vortices across the membrane filter, and wherein the means for comparing includes means for reestablishing steady state operation after the transmembrane pressure has been reduced.

21. The system as set forth in claim 18 above, wherein the threshold is set in the range of 135 to 165 mm Hg, wherein the Taylor number is in the range of 100 to 250, wherein the blood inlet rate is about 100 liters per minute and the membrane filter area is selected to provide two to three units of plasma in less than 45 minutes.

22. The system as set forth in claim 21 above, wherein the membrane filter has a relatively smooth surface, with surface protrusions no greater than about the pore size, wherein the membrane filter is disposed on the rotor, and wherein the blood inlet means and cell concentrate outlet means are space apart to provide flow against gravity forces.

23. The system as set forth in claim 22 above, wherein the membrane filter area is approximately 37 cm$^2$, the rotor diameter is approximately 2.5 cm, the annular gap is in the range of 0.018" (0.0457 cm) to 0.030" (0.0762 cm) and the rotational velocity of the rotor is less than about 3600 rpm.

24. The system as set forth in claim 23 above, wherein the shear rate is about 7500/sec, the rotational velocity is in the range of 3000-3600 rpm, the transmembrane pressure is about 148 mm Hg, the Taylor number is about 180 to 200, and pore size is in the range of 0.8 to 1.0 microns.

25. A system for filtering a cellular suspension passing between a rotating spinner and an outer shell without clogging a filter membrane on one of the surfaces comprising:

means for establishing a plurality of annular vortices in the suspension about the spinner and adjacent the membrane;

means for sensing the transmembrane pressure while maintaining a desired extraction rate of filtrate through the membrane;

means for comparing the transmembrane pressure to a transmembrane pressure value calculated to achieve extraction of filtrate with desired membrane efficiency and without substantial damage to the cellulose components; and means for reducing the extraction rate of filtrate while maintaining the vortex action to clean the membrane when the transmembrane pressure rises above the calculated value.

26. The system as set forth in claim 25 above wherein said means for reducing the filtrate extraction rate includes means for increasing fluid flow past the rotating spinner and the outer shell when the transmembrane pressure extends the calculated value, thereby causing the desired reduction in filtrate flow rate.

27. The system as set forth in claim 25 above wherein the desired filtrate extraction rate is maintained substantially constant when the transmembrane pressure is below the calculated value.

28. The system as set forth in claim 25 above and further including means for introducing a rinsing fluid between the rotating spinner and the outer shell while the filtrate extraction rate is reduced to assist in cleaning the membrane.

29. A system for filtering a cellular suspension, comprising:

a housing body having a hollow interior and an inner surface including a plurality of surface grooves;

rotor means rotatable within the housing body, the rotor means having an outer surface spaced from the inner surface of the housing body;

means for feeding the fluid suspension into the space between the rotor means, and the inner surface of the housing body;

filter membrane means disposed on the inner surface of the housing body for passing the filtrate to the surface grooves in the housing body;

conduit means in the housing body in communication with the surface grooves in the housing body for collecting filtrate passing therethrough; and means on said housing body for accessing the inner surface thereof comprising a split housing body having at least two split-apart body parts and means for releasably coupling the split body parts together and means for releasably attaching the filter membrane to the split body parts when split apart.

30. A system for filtering a suspension having a cellular component subject to trauma when stressed comprising:

a stationary housing body having a hollow interior and an inner surface;

rotor means rotatable within the housing body, the rotor means having an outer surface spaced from the inner surface of the housing body;

means for feeding the fluid suspension into the space between the rotor means and the inner surface of the housing body;

microporous filter membrane means disposed on the inner surface of the housing body for passing the filtrate to the inner surface of the housing body;

conduit means in the housing body in communication with the inner surface of the housing body for collecting filtrate passing through the filter membrane means; and means coupled to the rotor means for driving the rotor means at a rate selected to establish annular vortices about the rotor means, the annular vortices substantially filling the space between the rotor means and the housing body without causing substantial trauma to the cellular components.

31. A system for filtering a suspension containing at least one cellular blood component, comprising:

a stationary housing body having a hollow interior and an inner surface;

rotor means rotatable within the housing body, the rotor means having an outer surface spaced from the inner surface of the housing body;

means for feeding the fluid suspension into the space between the rotor means and the inner surface of the housing body;

microporous filter membrane means disposed on the inner surface of the housing body for passing the filtrate to the inner surface of the housing body;

conduit means in the housing body in communication with the inner surface of the housing body for collecting filtrate through the filter membrane means; and means coupled to the rotor means for driving the rotor means at a rate selected to establish annular vortices about the rotor means, the annular vortices substantially filling the space between the rotor means and the housing body without causing substantial damage to the cellular blood component.

32. A system for filtering a cellular suspension, comprising:

a housing body having a hollow interior and an inner surface;

rotor means rotatable within the housing body, the rotor means having an outer surface spaced from the inner surface of the housing body;

means for feeding the fluid suspension into the space between the rotor means and the inner surface of the housing body;

filter membrane means disposed on the inner surface of the housing body for passing the filtrate to the inner surface of the housing body;

conduit means in the housing body in communication with the inner surface of the housing body for collecting filtrate passing through the filter membrane means;

means coupled to the rotor means for driving the rotor means at a rate selected to establish annular vortices about the rotor means substantially filling the space between the rotor means and the housing body, and the housing body also includes means for accessing the inner surface comprising a split housing body having at least two split apart body parts and means for releasably coupling the split body parts together, the housing body further including means for releasably attaching the filter membrane means to the inner surface when split body parts are apart.

33. A system for filtering a suspension having a cellular component subject to trauma when stressed, comprising:

a housing body having a hollow interior and an inner surface;

rotor means rotatable within the housing body, the rotor means having an outer surface spaced from the inner surface of the housing body;

means for feeding the fluid suspension into the space between the rotor means and the inner surface of the housing body;

microporous filter membrane means disposed on the inner surface of the housing body for passing the filtrate to the inner surface of the housing body;

conduit means in the housing body in communication with the inner surface of the housing body for collecting filtrate passing through the filter membrane means;

means coupled to the rotor means for driving the rotor means at a rate selected to establish annular vortices about the rotor means, the annular vortices substantially filling the space between the rotor means and the housing body without causing substantial trauma to the cellular components; and the housing body also includes means for accessing the inner surface comprising a split housing body having at least two split apart body parts and means for releasably coupling the split body parts together, the housing body further including means for releasably attaching the microporous filter membrane means to the inner surface when split body parts are apart.

34. A system for filtering a suspension containing at least one cellular blood component, comprising:

a housing body having a hollow interior and an inner surface;

rotor means rotatable within the housing body, the rotor means having an outer surface spaced from the inner surface of the housing body;

means for feeding the fluid suspension into the space between the rotor means and the inner surface of the housing body;

microporous filter membrane means disposed on the inner surface of the housing body for passing the filtrate to the inner surface of the housing body;

conduit means in the housing body in communication with the inner surface of the housing body for collecting filtrate passing through the filter membrane means;

means coupled to the rotor means for driving the rotor means at a rate selected to establish annular vortices about the rotor means, the annular vortices substantially filling the space between the rotor means and the housing body without causing substantial damage to the cellular blood component, and the housing body also includes means for accessing the inner surface comprising a split housing body having at least two split apart body parts and means for releasably coupling the split body parts together, the housing body further including means for releasably attaching the microporous filter membrane means to the inner surface when split body parts are apart.

35. A system according to claim 1, 29, 30, 31, 32, 33 or 34 wherein the rotor means ia free of filter membrane means.

* * * * *